US012806163B2

(12) United States Patent
Thakkar et al.

(10) Patent No.: US 12,806,163 B2
(45) Date of Patent: Nov. 24, 2026

(54) COMPOSITION TO IMPROVE NUTRITIONAL CONTENT OF HUMAN BREAST MILK

(71) Applicant: SOCIETE DES PRODUITS NESTLE S.A., Vevey (CH)

(72) Inventors: Sagar Thakkar, La Tour-de-Peilz (CH); Tinu Mary Samuel, La Tour-de-Peilz (CH); Francesca Giuffrida, Mezieres (CH)

(73) Assignee: Societe des Produits Nestle S.A., Vevey (CH)

( * ) Notice: Subject to any disclaimer, the term of this patent is extended or adjusted under 35 U.S.C. 154(b) by 226 days.

(21) Appl. No.: 18/695,446

(22) PCT Filed: Sep. 26, 2022

(86) PCT No.: PCT/EP2022/076665
§ 371 (c)(1),
(2) Date: Mar. 26, 2024

(87) PCT Pub. No.: WO2023/052295
PCT Pub. Date: Apr. 6, 2023

(65) Prior Publication Data

US 2025/0332134 A1 Oct. 30, 2025

(30) Foreign Application Priority Data

Sep. 28, 2021 (EP) .................................... 21199539

(51) Int. Cl.

| | |
|---|---|
| ***A61K 31/202*** | (2006.01) |
| ***A23L 33/00*** | (2016.01) |
| ***A61K 31/07*** | (2006.01) |
| ***A61K 31/4415*** | (2006.01) |
| ***A61K 31/51*** | (2006.01) |
| ***A61K 31/519*** | (2006.01) |
| ***A61K 31/525*** | (2006.01) |
| ***A61K 31/675*** | (2006.01) |
| ***A61K 31/7032*** | (2006.01) |
| ***A61K 33/42*** | (2006.01) |

(52) U.S. Cl.
CPC ............ *A61K 31/202* (2013.01); *A23L 33/40* (2016.08); *A61K 31/07* (2013.01); *A61K 31/4415* (2013.01); *A61K 31/51* (2013.01); *A61K 31/519* (2013.01); *A61K 31/525* (2013.01); *A61K 31/675* (2013.01); *A61K 31/7032* (2013.01); *A61K 33/42* (2013.01)

(58) Field of Classification Search
CPC .. A61K 31/202; A61K 31/07; A61K 31/4415; A61K 31/51; A61K 31/519; A61K 31/525; A61K 31/675; A61K 31/7032; A61K 33/42; A23L 33/40; A23L 33/115; A23L 33/15; A23L 33/12; A23L 33/155; A23V 2002/00
See application file for complete search history.

(56) References Cited

U.S. PATENT DOCUMENTS

2017/0332691 A1* 11/2017 Ameye et al.
2021/0227845 A1 7/2021 Berg et al.

FOREIGN PATENT DOCUMENTS

CN 102665428 A 9/2012
WO 2009051502 A1 4/2009

OTHER PUBLICATIONS

Chinese Office Action for Appl No. 202280065866.3 dated Oct. 22, 2025, 9 pages.
"Dietary Reference Intakes for China", Chinese Nutrition Society, 2023 Edition, 10 Pages.
Chinese Office Action for Appl No. 202280065866.3 dated Jun. 23, 2026, 11 pages.

* cited by examiner

*Primary Examiner* — Robert A Wax
*Assistant Examiner* — Kimberly Barber
(74) *Attorney, Agent, or Firm* — K&L Gates LLP

(57) ABSTRACT

A maternal supplement or human milk fortifier composition comprising at least one nutrientselected in the list consisting of: ALA, DHA, EPA, vitamin A, thiamine, thiamine monophosphate, vitamin B2, vitamin B6, vitamin B9, calcium and phosphorus, GD3, GM3. Said maternal supplement or human milk fortifier composition is specifically tailored or adapted for a woman who has delivered via C-section who is breast feeding. Said maternal supplement or human milk fortifier composition is beneficial to provide adequate nutrition to a woman who has delivered via C-section and promote associated health benefits.

12 Claims, No Drawings

COMPOSITION TO IMPROVE NUTRITIONAL CONTENT OF HUMAN BREAST MILK

CROSS REFERENCE TO RELATED APPLICATIONS

The present application is a National Stage of International Application No. PCT/EP2022/076665, filed on Sep. 26, 2022, which claims priority to European Patent Application No. 21199539.4, filed on Sep. 28, 2021, the entire contents of which are being incorporated herein by reference.

TECHNICAL FIELD OF THE INVENTION

The present invention relates to a maternal supplement composition which may be provided to women who have given birth via caesarean section. In particular, the present invention relates to a maternal supplement composition specifically tailored or adapted for women who have given birth via caesarean section. The invention furthermore relates to the use of said maternal supplement composition.

BACKGROUND OF THE INVENTION

Caesarean section rates are increasing around the world; whilst the international health care community considers that an ideal caesarean section rate to be between 10 to 15%, it is reported that today's rate may be higher than 30% in many countries (Boerma T. et al., Lancet: 2018:392 (10155): 1341-1348).

The reasons for caesarean sections vary. In many cases a caesarean section is medically indicated and therefore necessary to save the life of the baby or the mother, this may be because a vaginal birth is not possible, e.g. because of failure of the normal progression of labor. In other cases, a caesarean section may be elective and performed at the request of pregnant women or family.

Regardless of the reason for a caesarean section, infants born in this way are reported to be at an increased risk of suffering from a variety of health complaints in infancy, childhood, and even later in life. The reasons for this increased risk are not clear. However, given the increasing frequency of caesarean sections, there is a need to identify factors that may contribute to this risk and to address them.

The inventors have identified a factor that may contribute to this risk. In particular the inventors have found that the concentration of several nutrients found in human breast milk (hereinafter "HM") produced by mothers to infants born via caesarean section (hereinafter C-section) may differ from the concentration of the same nutrients found in HM produced by mothers to infants born by vaginal delivery. More particularly the inventors have found that the concentration of certain specific Human Milk Oligosaccharides (hereinafter "HMOs"), vitamins, fatty acids, gangliosides and minerals found in HM produced by mothers to infants born via vaginal delivery may be higher than the concentration of the same specific HMOs, vitamins, fatty acids, gangliosides and minerals found in HM produced by mothers to infants born via C-section delivery.

Accordingly, there is need for a maternal supplement composition which may be provided to women who have given birth via caesarean section comprising one or more nutrients that can be used to fortify HM produced by mothers who have given birth via C-section, and thereby to optimise the intake of one or more nutrients, such as vitamins, fatty acids, gangliosides and minerals, in infants delivered via C-section.

SUMMARY OF THE INVENTION

The inventors have surprisingly found that the concentration of certain specific nutrients in HM produced by mothers to infants born via vaginal delivery may be higher than the concentration of the same nutrients found in HM produced by mothers to infants born via C-section. An optimal intake of these compounds in infancy is believed to be necessary to ensure optimum health and development. Providing one or more nutrients that were observed to be decreased to a woman who has delivered by C-section allows restoring the amounts of those nutrients in HM of those mothers to a level at least comparable to the concentrations of the same nutrients found in HM produced by mothers to infants born via vaginal delivery. Considering these findings, the inventors have developed a maternal supplement for women who have given birth via caesarean section comprising at least one or more of such nutrients. Namely, the specific nutrients above mentioned are: alpha-linolenic fatty acid (hereinafter "ALA"), docosahexaenoic acid (hereinafter "DHA"), eicosapentaenoic acid (hereinafter "EPA"), vitamin A, thiamine, thiamine monophosphate, vitamin B2, vitamin B6, vitamin B9, phosphorus, and gangliosides.

The invention is set out in the claims and in the detailed description included herein.

In one aspect, the present invention provides for a maternal supplement composition comprising at least one nutrient selected in the group consisting of:

- alpha linolenic acid (ALA), for example in a daily amount ranging from 0.1 to 2.6 mg;
- docosahexaenoic acid (DHA), for example in a daily amount ranging from 35 to 700 mg;
- eicosapentanoic acid (EPA), for example in a daily amount ranging from 10 to 200 mg,
- vitamin A, for example in a daily amount ranging from 130 to 3000 μg, thiamine, for example in a daily amount ranging from 0.14 to 2.8 mg;
- thiamine monophosphate, for example in a daily amount ranging from 0.14 to 2.8 mg;
- vitamin B2, for example in a daily amount ranging from 0.16 to 3.2 mg;
- vitamin B6, for example in a daily amount ranging from 0.2 to 100 mg;
- vitamin B9, for example in a daily amount ranging from 50 to 1000 μg;
- phosphorus, for example in a daily amount ranging from 70 to 4000 mg;
- gangliosides, for example in a daily amount ranging from 0.1 to 12.6 mg; and or any combination thereof.

In another aspect, the present invention provides for a maternal supplement as above describe wherein the supplement is specifically tailored or adapted to supplement or fortify the HM of a woman who has delivered via C-section. The women (or mothers) who have delivered via C-section are breast feeding, at least partially. The purpose is to modify (i.e. to fortify) the HM of the mother who has delivered by C-section to address nutrient inadequacy in HM of those women. The amount of nutrients in HM is indeed modifiable when supplemented to the mother (Samuel et al., Front Nutr.: 2020: 7: 576133). Thereby it is ensured that an infant born via C-section fed with HM fortified by the maternal supplement according to the present invention does not receive less of one or more of the above-mentioned nutrients than an infant born via vaginal delivery.

In another aspect, the present invention also provides for a maternal supplement composition as above described for use in preventing nutrient inadequacy in HM produced by a woman who has delivered via C-section. In one embodiment, the maternal supplement composition is provided to a woman who has delivered via C-section.

In yet another embodiment, the present invention provides for the use of a maternal supplement composition as above described to i) prevent sub-optimal growth and development;
ii) prevent and/or treat inflammatory process;
iii) promote cognitive development; and/or
iv) promote immunity development in an infant born via C-section.

Infants born via C-section, compared with those born vaginally, are at increased risk of altered immune development, allergy, atopy, asthma, and reduced diversity of the intestinal gut microbiome (Sandal! J. et al., Lancet: 2018: 392 (10155): 1349-1357). Recent evidence also suggests that C-section may be associated with neurodevelopmental outcomes such as a shift in brain development, at least during early infancy (e.g. significantly lower white matter development in widespread brain regions and significantly lower functional connectivity in the brain default mode network) ((Deoni SC. et al., Am. J. Neuroradiol.: 2019: 40 (1): 169-177).

Accordingly, infants born via C-section are in general at increased risk of suboptimal growth and development.

In a further aspect, the present invention also provides for a maternal supplement composition as above described for use in preventing sub-optimal growth and development in an infant born via C-section.

As previously discussed, one factor that may contribute to suboptimal growth and development in infant born via C-section is that the concentration of several nutrients found in HM produced by mothers to infants born via C-section may differ from the concentration of the same nutrients found in HM produced by mothers to infants born by vaginal delivery. An optimal intake of these nutrients in infancy and/or early childhood is believed to be necessary to ensure optimum health and development. Therefore, providing to mothers who have delivered via C-section a maternal supplement composition that delivers one or more nutrient that are decreased in HM produced by mothers to infants born via C-section may address the nutrient inadequacy in the HM of those mothers. Consequently, the risk of sub-optimal growth and development in the infant born via C-section is prevented by the fortification of HM produced by mother who have delivered via C-section.

As above discussed, certain omega-3 fatty acids have also been found by the present inventors to be present in decreased amounts in the human breast milk of women who delivered via C-section.

Omega-3 fatty acids ALA, EPA and DHA act as precursor of some inflammation resolving compounds such as prostaglandins, leukotrienes and resolvins (Ishiara T. et al., International Immunology: 2019: 31 (9): 559-567). The observation that ALA and DHA were present at lower levels in HM produced by mothers who have delivered via C-section indicates that ALA and DHA were presumably converted to these protective molecules and have therefore reduced availability for infants by HM. Therefore, providing extra ALA, EPA and DHA (omega-3 fatty acids) to mothers who have delivered via C-section may address the deficiency of such nutrients in the HM, thereby preventing the risk of inflammatory process in an infant born via C-section.

In a still further aspect, the present invention provides for a maternal supplement composition as herein described for use in preventing nutrient inadequacy in HM of a woman who has delivered via C-section, thereby preventing and/or treating inflammatory process in an infant born via C-section.

In another aspect of the present invention, there is provided a maternal supplement composition for use in fortifying or supplementing the amount of one or more nutrients that were observed to be decreased in HM, and preferably HM produced by a woman who has delivered via C-section, thereby preventing and/or treating inflammatory process in an infant born via C-section As above discussed, certain omega-3 fatty acids have also been found by the present inventors to be present in decreased amounts in the HM of women who delivered by C-section.

Among omega 3 fatty acids, ALA is essential and is the most abundant omega-3 fatty acid in the diet. ALA is the precursor of long-chain omega-3 polyunsaturated fatty acids (PUFAs) including EPA (20:5n-3), docosapentaenoic acid (DPA; 22:5n-3), and DHA (22:6n-3) (Leonarda et al., Progress in Lipid Research: 2004: 43: 36-5). These long-chain omega-3 PUFAs can be also consumed directly from food sources such as oily fish. Animal studies demonstrate that consuming a diet lacking in omega-3 fatty acids during pregnancy and lactation results in neurological abnormalities in offspring, e.g. impairments of cognitive and visual function (Brenna J. T. et al., Maternal and Child Nutrition: 2011: 7 (s2): 59-79; Lauritzen et al., Progress in Lipid Research: 2001: 40: 1-94) and that these impairments are associated with a reduction in brain DHA content. Therefore, providing extra ALA to mothers who have delivered via C-section may address the deficiency of such nutrient in HM, thereby promoting cognitive development in an infant born via C-section (Miles EA. Et al. Nutrients: 2017: 9(7):784; Hoff S. et al., Eur. J. Clin. Nutr.: 2005: 59: 1071-1080).

In a still further aspect, the present invention provides for maternal supplement composition as herein described for use in preventing nutrient inadequacy in HM of a woman who has delivered via C-section, thereby promoting cognitive development in an infant born by C-section.

In yet another aspect of the present invention, there is provided a maternal supplement composition for use in fortifying or supplementing the amount of one or more nutrients that were observed to be decreased in HM, and preferably HM produced by a woman who has delivered via C-section, thereby promoting cognitive development in an infant born by C-section.

A link has been demonstrated between high intake of omega-3 PUFAs and increased incidence of allergic diseases. Because PUFAs are involved in cell signalling, gene expression and cellular function through membrane-mediated actions, PUFAs can modulate immune cell function, including inflammatory component. Ecosanoids, a proinflammatory molecules synthesised from 20-carbons PUFAs, are thought to be involved in clinical manifestations of allergic diseases (Miles E. A. et al., Nutrients: 2017: 9(7): 78). These proinflammatory molecules are counter interacted by the inflammation resolving molecules synthesized in the pathways of omega-3 fatty acids, therefore generating a biological plausible mechanism by which omega-3 PUFAs may protect against allergic sensitisation and manifestations. Some evidence suggests that a higher intake of n-3 PUFA is associated with a decreased risk of allergic sensitisation and allergic rhinitis (S. Hoff et al., Eur. J. Clinical Nutr.: 2005: 59: 1071-1080). Epidemiological evidence suggests that consumption of fish oil during pregnancy reduces allergic outcomes in infants and children.

Essential vitamins and minerals have long been known to play a role in innate and adaptive immune responses and therefore influence the development of allergic diseases in humans. Vitamins A and D has been extensively studied in preclinical models for their role in development of allergic diseases and show a promising result (Hufnagl K. et al., Allergo. J. Int.: 2018: 27(3):72-8; Matheu V. et al., Nutr. Metab.: 2009: 6: 44; Marmsjo K. et al., The American Journal of Clinical Nutrition: 2009: 90 (6): 1693-1698). Furthermore, children for whom an intake of multivitamin at or before the age of 4 years old was reported showed a decreased risk of sensitization to food allergens and tendencies toward inverse associations with allergic rhinitis (Marmsjö et al., the American J. Clinic) Nutr.: 2009: 90 (6): 1693-8).

Therefore, providing extra ALA, EPA and DHA (omega-3 fatty acids), essential vitamins and minerals to mothers who have delivered via C-section may address the deficiency of such nutrients in the human breast milk, thereby promoting immunity development, and/or reducing allergic outcome in infant born via C-section.

In a still further aspect, the present invention provides for a maternal supplement composition as herein described for use in preventing nutrient inadequacy in HM of a woman who has delivered via C-section, thereby promoting immunity development in infants born via C-section.

In yet another aspect of the present invention, there is provided a maternal supplement composition for use in fortifying or supplementing the amount of one or more nutrients that were observed to be decreased in HM, and preferably HM produced by a woman who has delivered via C-section, thereby promoting immunity development in infants born via C-section.

In another aspect, the present invention provides for a maternal supplement composition as described therein for use in preventing nutrient inadequacy in HM of a woman who has delivered via C-section, thereby reducing allergic outcome in infant born via C-section.

In a still further aspect, the present invention provides for a maternal supplement composition for use in fortifying or supplementing the amount of one or more nutrients that were observed to be decreased in HM, and preferably HM produced by a woman who has delivered via C-section, thereby reducing allergic outcome in infant born via C-section.

The maternal supplement composition would be tailored or adapted to women (or mothers) who have delivered via C-section and are breast feeding, at least partially. The purpose is to modify (i.e. to fortify) the HM of the mother who has delivered by C-section to address nutrient inadequacy in HM of those women. The amount of nutrients in HM is indeed modifiable when supplemented to the mother (Samuel et al., Front Nutr.: 2020: 7: 576133). Thereby it is ensured that an infant born via C-section fed with HM fortified by the maternal supplement according to the present invention does not receive less of one or more of the above-mentioned nutrients than an infant born via vaginal delivery.

The infant may be selected from the group consisting of: a preterm infant and a term infant. In one embodiment, the infant is an infant born via C-section.

The maternal supplement composition may further comprise one or more ingredient selected from the group consisting of additional vitamins, additional minerals, protein, additional carbohydrates, and probiotics.

Also provided is a method of mitigating nutrient inadequacy in a woman who has delivered via C-section, said method comprising:

i) identifying the gap in certain nutrients between the human breast milk composition from mothers who have delivered via C-section and the human breast milk composition from mothers who have delivered vaginally; and
ii) providing a maternal supplement according to the present invention to mitigate the identified nutritional inadequacies in a woman who has delivered via C-section

DETAILED DESCRIPTION

Various preferred features and embodiments of the present invention will now be described by way of non-limiting examples. The skilled person will understand that they can combine all features of the invention disclosed herein without departing from the scope of the invention as disclosed.

Definitions

The expressions "maternal supplement" or "maternal supplement composition" can be used interchangeably and refer to a composition which is intended to supplement the general diet of a mother. The maternal supplement according to the present invention may be provided in different formats (such as drops, powder, oral solution) to be consumed as such.

In one embodiment, the maternal supplement is specifically tailored or adapted to fortify the HM of a woman who has delivered via C-section. In another embodiment, the woman who has delivered via C-section is breast-feeding, at least partially.

The term "supplement" refers to a foodstuff or a composition containing one or more nutrients intended to supplement the diet. A supplement may be liquid or solid (e.g. powder) composition and may be suitable for mixing with liquids such as with water.

The terms "fortify", "fortifying", "supplement", "supplementing", "complement" and "complementing" can be used interchangeably within the context of the present invention and should be understood as completing or supplementing the decreased amounts of one or more nutrients that were observed to be decreased in HM produced by mothers who have delivered via C-section when compared to the amounts of the same nutrients found in HM produced by mothers to infants born via vaginal delivery.

Within the context of the present invention, the terms "nutrient inadequacy" indicates that the total amount of one or more nutrient in HM of a woman who has delivered via C-section is below (i.e. is decreased) the amount of those nutrient in a woman who has delivered via vaginal delivery.

Within the context of the present invention, the expression "prevent nutrient inadequacy" should be understood to include prevention of inadequacies of the nutrients in HM of a woman who has delivered via C-section, as well as reduction of the risk of nutrient inadequacies in HM of a woman who has delivered via C-section.

The terms "serving" or "dosage unit" within the context of the present invention indicates the amount of maternal supplement composition which provided as an individual dose unit or which is to be consumed at an individual eating or feeding occasion according to the indication provided on the package of the maternal supplement composition.

The term "C-section" as used herein refers to a caesarean section or caesarean delivery in general. C-section is the surgical procedure by which a baby is delivered through an incision in the mother's abdomen. The C-section may have been a planned/elective C-section, or an emergency C-section.

The term "infant" as used herein, refers to a human of less than about 6 months of age. The term includes preterm infants, premature infants, small for gestational age (SGA) infants and/or infant with low birth weight (LBVV).

The expressions "preterm infant" or "premature infant" can be used interchangeably. They should be understood as comprising an infant who is not born at term. Generally, they refer to infant born alive prior to 37 weeks of gestation/pregnancy.

The expression "small for gestational age infant" as used herein, refers to an infant who is smaller in size than normal for their gestational age at birth, most commonly defined as a weight below the 10th percentile for the gestational age. In some embodiments, SGA may be associated with intrauterine growth restriction (IUGR), which refers to a condition in which a foetus is unable to achieve its potential size.

The expression "low birth weight infant" as used herein refers to an infant that has a body weight under 2500 g at birth. It therefore encompasses:

- an infant who has/had a body weight from 1800 to 2500 g at birth (usually called "low birth weight" or LBVV)
- an infant who has/had a body weight from 1000 to 1800 g at birth (called "very low birth weight" or VLBW)
- an infant who has/had a body weight under 1000 g at birth (called "extremely low birth weight" or ELBW)

An infant or young child with low birth weight may or may not be preterm, and similarly, an infant or young child who is small for gestational age may or may not be preterm.

The term "child" as used herein, refers to a human from about 6 months to about 7 years of age, for example, between 1 and 3 years of age.

The expression "sialylated oligosaccharide" as used herein refers to an oligosaccharide having a sialic acid (such as N-acetylneuraminic acid and/or N-glycolylneuraminic acid) residue.

The expression "N-acetylatedoligosaccharide" as used herein refers to an oligosaccharide having at least one hexose carrying an N-acetyl residue.

The expression "fucosylated oligosaccharide" as used herein refers to an oligosaccharide having a fucose residue.

The terms "promote", "promotion" and "promoting" can be used interchangeably. They should be understood as comprising support or help to the health in an individual, for example to support or help the development or growth of an individual. The individual may not suffer from a disease but may be susceptible to the development of unhealthy conditions, for example later in life.

The terms "treat", "treating" or "treatment" as used therein may mean both prophylactic or preventive treatment (i.e. that prevent and/or slow the development of a targeted pathologic condition or disorder) and curative, therapeutic or disease-, modifying treatment, including therapeutic measures that cure, slow down, lessen symptoms of, and/or halt progression of a diagnosed pathologic condition or disorder. It may include treatment of patients at risk of contracting a disease or suspected to have contacted a disease, as well as patients who are ill or have been diagnosed as suffering from a disease or a medical condition. The terms "treat", "treating" or "treatment" do not necessarily imply that a subject is treated until total recovery. The terms "treat", "treating" or "treatment" also refer to the maintenance and/or promotion of health in an individual not suffering from a disease but who may be susceptible to the development of unhealthy condition. The terms "treat", "treating" or "treatment" are also intended to include potentiation or otherwise enhancement of one or more prophylactic or therapeutic measures. As an embodiment, the term "treatment" indicates prophylactic or preventive treatment.

Within the context of the present invention, the expressions "in the prevention and/or treatment of inflammatory process", "to prevent and/or treat inflammatory process" or "for the prevention and/or the treatment of inflammatory process" can be used interchangeably. They should be understood as comprising the decrease of the duration of inflammatory process, of the severity of inflammatory process. These expressions also encompass the relieve of the symptoms induced by inflammatory process, such as pain, stress, tiredness, and/or the decrease of complications caused by inflammatory process. The term "inflammatory process" can be understood as an inflammatory response (i.e. inflammation) that may occur when tissues are injured by bacteria, trauma, toxins, heat or any other cause.

Within the context of the present invention, the expression "cognitive development" should be understood as comprising how an individual, for example an infant or a child, learns to think, reason, and use language. It is the development of knowledge, skills, problem solving and dispositions, which help individuals to think about and understand the world around them. Among the areas of cognitive development are information processing, intelligence, reasoning, language development and memory. Infants are aware of their surroundings and show interest in the exploration of their environment from the time they are born. From birth, the infants start to actively learn, to gather, sort and process information from their surroundings using the data to develop perception and thinking skills.

Within the context of the present invention, the expression "immunity development" as used herein refers to the development of the immune system by adaptation in response to antigen stimulus, which starts at birth and continues throughout life. Immunity is developing and still to reach maturity in infants and children.

Within the context of the present invention, the term "allergy" comprises food allergy, atopic dermatitis, allergic asthma, and/or allergic rhinitis. For example, allergy is a food allergy.

The Maternal Supplement Composition

In a first aspect of the present invention there is provided a maternal supplement composition comprising at least one nutrient selected in the group consisting of: ALA, DHA, EPA, vitamin A, thiamine, thiamine monophosphate, vitamin B2, vitamin B6, vitamin B9, phosphorus, gangliosides or any combination thereof.

In one embodiment, the maternal supplement composition is tailored or adapted to fortify or supplement the human breast milk of a woman who has delivered by C-section, thereby addressing nutrient inadequacies. A maternal supplement composition, as disclosed herein, may be considered as specifically tailored or adapted to fortify the human breast milk of a woman who has given birth via C-section if it comprises at least one nutrient selected in the group consisting of: ALA, DHA, EPA, vitamin A, thiamine, thiamine monophosphate, vitamin B2, vitamin B6, vitamin B9, phosphorus, and gangliosides, as described herein. Said maternal supplement composition may, for example, comprise said at least one or more nutrient selected in the group consisting of: ALA, DHA, EPA, vitamin A, thiamine, thiamine monophosphate, vitamin B2, vitamin B6, vitamin B9, phosphorus, and gangliosides, in an amount sufficient to address the deficiency of such at least one nutrient in the human breast milk of mothers who have given birth via C-section in comparison to mothers who have given birth vaginally. A sufficient amount of a nutrient may for example be an amount equal to or greater than an amount that a mother would produce to an infant born via vaginal delivery, or may for example, be any amount that is equal to or higher than the difference found in the concentration, e.g. averages, in human milk produced by women who have given birth via vaginal delivery and women who have given birth via C-section delivery. Said maternal supplement composition may be a delivery mode specific maternal supplement. For example, said maternal supplement may be sold for use in women who have delivered via C-section. Said maternal supplement may be marketed as being for use to supplement the general diet of a women who have given birth via C-section. For example, said maternal supplement may be sold specifically for use in women who have given birth via C-section. Said maternal supplement may be marketed as a being for use to fortify the breast milk of women who have given birth via C-section.

In one embodiment of the present invention, the maternal supplement composition of the present invention comprises at least one nutrient selected in the group consisting of: ALA, DHA, EPA, vitamin A, thiamine, thiamine monophosphate, vitamin B2, vitamin B6, vitamin B9, phosphorus, and gangliosides, respectively in the amounts reported in Table I below.

TABLE I

| Nutrients | Daily amount to be supplemented |
|---|---|
| ALA (18:3 n-3) | 0.1-2.6 g |
| DHA (22:6 n-3) | 35-700 mg |
| EPA (20:5n-3) | 10-200 mg |
| Vitamin A | 130-3000 lug |
| Thiamine (vitamin b1) | 0.14-2.8 mg |
| Thiamine monophosphate | 0.14-2.8 mg |
| Vitamin B2 (Riboflavin) | 0.16-3.2 mg |
| Vitamin B6 | 0.2-100 mg |
| Vitamin B9 | 50-1000 lug |
| Phosphorus | 70-4000 mg |
| Gangliosides | 0.1-12.6 mg |

In one embodiment, the maternal supplement composition according to the present invention may be administered in 1, 2, 3 or 4 daily servings or dosage units to provide the total daily amounts of the nutrients as above described. As it will be apparent to a person skilled in the art, to calculate the amount of each nutrient contained in each serving or dosage unit of the maternal supplement according to the present invention, the daily amount as above reported will be divided by 1, 2, 3 or 4 respectively.

The concentrations listed herein, when expressed as mg/mL, refer to concentrations after a composition has been reconstituted or mixed with water or milk.

In an embodiment of the present invention the maternal supplement composition is tailored or adapted for a woman who has delivered by C-section. In one embodiment, the woman who has delivered via C-section is breast feeding her infant. In another embodiment, the woman who has delivered via C-section is partially breast feeding her infant. In another embodiment of the present invention the infant born via C-section is of an age selected from the group consisting of; up to 6 months of age, up to 5 months of age, up to 4 months of age, up to 3 months of age, up to 2 months of age, up to 1 month of age, up to 3 weeks of age, up to 2 weeks of age, up to 1 week of age. For example, the maternal supplement composition may be tailored or adapted to fortify breast milk produced for an infant up to 1 month of age e.g. up to 2 weeks of age.

In another embodiment, the infant is a child of at least 6 months of age, such as a child of 6 month of age, a child of 7 months of age, a child of 8 months of age, a child of 9 months of age, a child of 10 months of age, a child of 11 months of age, a child of 12 months of age. In yet another embodiment, the child is between 6 and 24 months of age, or is a child between 6 and 18 months of age, or is a child between 6 and 12 months of age. The child may have been born via C-section In one embodiment, the infant is selected from the group consisting of preterm infants and term infants.

In one embodiment of the present invention, it is provided a maternal supplement composition comprising at least one nutrient selected in the group consisting of:

alpha linolenic acid (ALA) in a daily amount ranging from 0.1 to 2.6 g;

docosahexaenoic acid (DHA) in a daily amount ranging from 35 to 700 mg;

eicosapentanoic acid (EPA) in a daily amount ranging from 10 to 200 mg; vitamin A in a daily amount ranging from 130 to 3000 μg;

thiamine in a daily amount ranging from 0.14 to 2.8 mg;

thiamine monophosphate in a daily amount ranging from 0.14 to 2.8 mg;

vitamin B2 in a daily amount ranging from 0.16 to 3.2 mg;

vitamin B6 in a daily amount ranging from 0.2 to 100 mg;

vitamin B9 in a daily amount ranging from 50 to 1000 μg;

phosphorus in a daily amount ranging from 70 to 4000 mg; and gangliosides in a daily amount ranging from 0.1 to 12.6 mg;

or any combination thereof.

In a further embodiment, the present invention provides a maternal supplement composition as above described wherein the composition comprises:

alpha linolenic acid (ALA) in a daily amount ranging from 0.1 to 2.6 g;

docosahexaenoic acid (DHA) in a daily amount ranging from 35 to 700 mg;

eicosapentanoic acid (EPA) in a daily amount ranging from 10 to 200 mg; and which optionally comprises at least one nutrient selected in the group consisting of:

vitamin A, for example in a daily amount ranging from 130 to 3000 μg; 12 thiamine, for example in a daily amount ranging from 0.14 to 2.8 mg;

thiamine monophosphate, for example in a daily amount ranging from 0.14 to 2.8 mg;

vitamin B2, for example in a daily amount ranging from 0.16 to 3.2 mg;

vitamin B6, for example in a daily amount ranging from 0.2 to 100 mg;

vitamin B9, for example in a daily amount ranging from 50 to 1000 ρg, phosphorus, for example in a daily amount ranging from 70 to 4000 mg; and gangliosides, for example in a daily amount ranging from 0.1 to 12.6 mg;

or any combinations thereof.

In another embodiment, the present invention provides for a maternal supplement composition as herein described which comprises at least one nutrient selected in the group consisting of phosphorus, for example in a daily amount ranging from 70 to 4000 mg;

gangliosides, for example in a daily amount ranging from 0.1 to 12.6 mg;

and optionally comprises at least one nutrient selected in the group consisting of:

alpha linolenic acid (ALA), for example in a daily amount ranging from 0.1 to 2.6 g;

docosahexaenoic acid (DHA), for example in a daily amount ranging from 35 to 700 mg eicosapentanoic acid (EPA), for example in a daily amount ranging from 10 to 200 mg, vitamin A, for example in a daily amount ranging from 130 to 3000 μg;

thiamine, for example in a daily amount ranging from 0.14 to 2.8 mg;

thiamine monophosphate, for example in a daily amount ranging from 0.14 to 2.8 mg;

vitamin B2, for example in a daily amount ranging from 0.16 to 3.2 mg;

vitamin B6, for example in a daily amount ranging from 0.2 to 100 mg;

vitamin B9, for example in a daily amount ranging from 50 to 1000 [1 g;

or any combination thereof.

The maternal supplement composition of the invention can also comprise any other ingredients or excipients known to be employed in maternal supplements.

Non limiting examples of such ingredients include proteins, amino acids, carbohydrates, lipids, prebiotics or probiotics, essential fatty acids, nucleotides, nucleosides, vitamins, minerals and other micronutrients.

In an embodiment of the invention the maternal supplement composition further comprises one or more ingredients selected from the group consisting of additional vitamins, additional minerals, protein, additional carbohydrates, and probiotics.

Non limiting examples of proteins include casein, alpha-lactalbumin, whey, soy protein, rice protein, corn protein, oat protein, barley protein, wheat protein, rye protein, pea protein, egg protein, sunflower seed protein, potato protein, fish protein, meat protein, lactoferrin, serum albumin, immunoglobins, and combinations thereof.

Non limiting examples of amino acids include leucine, threonine, tyrosine, Isoleucine, arginine, alanine, histidine, isoleucine, proline, valine, cysteine, glutamine, glutamic acid, glycine, serine, arginine, lysine, methionine, phenylalanine, tryptophane, asparagine, aspartic acid, and combinations thereof.

Non limiting examples of digestible carbohydrates include lactose, saccharose, maltodextrin, starch, and combinations thereof.

Non limiting examples of lipids include palm olein, high oleic sunflower oil, high oleic safflower oil, canola oil, fish oil, coconut oil, bovine milk fat, and combinations thereof.

Non limiting examples of essential fatty acids include linoleic acid (LA) and polyunsaturated fatty acids (PUFAs). The compositions of the invention may further contain phospholipids such as sphingomyelin, phospholipids phosphatidylcholine, phosphatidylethanolamine, phosphatidylinositol, phosphatidylserine, and combinations thereof.

None limiting examples of non-digestible carbohydrates (prebiotics) include oligosaccharides optionally containing additional HMOs, fructose, galactose, mannose; dietary fibers, in particular soluble fibers, soy fibers; inulin; and combinations thereof. Preferred prebiotics are fructo-oligosaccharides (FOS), galacto-oligosaccharides (GOS), isomalto-oligosaccharides (IMO), xylo-oligosaccharides (XOS), arabino-xylo oligosaccharides (AXOS), mannan-oligosaccharides (MOS), oligosaccharides of soy, glycosylsucrose (GS), lactosucrose (LS), lactulose (LA), palatinose-oligosaccharides (PAO), malto-oligosaccharides, gums and/or hydrolysates thereof, pectins and/or hydrolysates thereof, and combinations of the foregoing.

The additional HMO may be a sialylated oligosaccharide, a fucosylated oligosaccharide, an N-acetylated oligosaccharide, or any combination thereof. The one or more HMO may for example be selected from the group consisting of; 2-fucosyllactose, 3'-fucosyllactose, 3'-sialyllactose, 6'-galactosyllactose, difucosyllacto-N-Hexose-a, fucosyllacto-N-hexose-III, Lacto-N-neotetraose, Lacto-N-fucosylpentaose-1, Lacto-N-fucosylpentaose-III, Lacto-N-fucosylpentaose-V, Lacto-N-hexaose (A), Lacto-N-Neodifucosylhexaose, Lacto-N-Neofucosylpentaose, Lacto-N-Tetraose, and any combination thereof.

The human milk fortifier composition may comprise an additional HMO in a range of 0.1 to 10000 mg/L.

Non limiting examples of probiotics include *Bifidobacterium, Lactobacillus, Lactococcus, Enterococcus, Streptococcus, Kluyveromyces, Saccharoymces, Candida*, in particular selected from the group consisting of *Bifidobacterium longum* ssp *longum, Bifidobacterium lactis, Bifidobacterium animalis, Bifidobacterium breve, Bifidobacterium longum* ssp *infantis, Bifidobacterium adolescentis, Lactobacillus acidophilus, Lactobacillus casei, Lactobacillus paracasei, Lactobacillus salivarius, Lactobacillus lactis, Lactobacillus rhamnosus, Lactobacillus johnsonfi, Lactobacillus plantarum, Lactobacillus salivarius, Lactobacillus reuteri protectis, Lactococcus lactis, Enterococcus faecium, Saccharomyces cerevisiae, Saccharomyces boulardii* or mixtures thereof, preferably selected from the group consisting of *Bifidobacterium longum* NCC3001 (ATCC BAA-999), *Bifidobacterium longum* NCC2705 (CNCM 1-2618), *Bifidobacterium longum* NCC490 (CNCM 1-2170), *Bifidobacterium lactis* NCC2818 (CNCM 1-3446), *Bifidobacterium breve* strain A, *Lactobacillus paracasei* NCC2461 (CNCM 1-2116), *Lactobacillus johnsonfi* NCC533 (CNCM 1-1225), *Lactobacillus rhamnosus* GG (ATCC53103), *Lactobacillus rhamnosus* NCC4007 (CGMCC 1.3724), *Enterococcus faecium* SF 68 (NCC2768; NCIMB10415), and combinations thereof.

In some embodiments, the maternal supplement composition according to the present invention comprises one or more probiotics selected from the group consisting of *Bifidobacterium longum* ssp *longum, Bifidobacterium lactis, Bifidobacterium animalis, Bifidobacterium breve, Bifidobacterium longum* ssp *infantis, Bifidobacterium adolescentis.*

In some embodiments, at least one, or at least two or more probiotics are included in the human milk fortifier composition according to the present invention in amount from about 101 to 1018 cfu (colony forming unit), such as 102 to 1015, 103 to 1012 105 to 1012 106 to 1012, 107 to 1012, 108 to 1012 or 109 to 1 012 cfu of each strain per g on a dry weight basis or per mL of the composition on a volume basis. In some embodiments, the human milk fortifier composition comprises 101, 102, 103, 104, 105, 106, 107, 108, 109, 1010, 1011, 1 012, 1 013, 1 014, 1015, 1016, 1017, or about 1018 cfu of one or more probiotics per g on a dry weight basis or per mL of the composition on a volume basis. In some other embodiments, the human milk fortifier composition comprises about 101 to about 102, 103, 104, 105, 106, 107, 108, 109, 1010, 1011, 1012, 1013, 1014, 1015, 1016, 1017, or about 1018 cfu of one or more probiotics per g on a dry weight basis or per mL of the composition on a volume basis.

Non limiting examples of nucleotides include cytidine monophosphate (CMP), uridine monophosphate (UMP), adenosine monophosphate (AMP), guanosine monophosphate (GMP), and combinations thereof.

Non limiting examples of additional vitamins and minerals include vitamin B2, vitamin E, vitamin K, vitamin C, vitamin D, folic acid, inositol, niacin, biotin, pantothenic acid, choline, iodine, iron, magnesium, copper, zinc, manganese, chloride, potassium, sodium, selenium, chromium, molybdenum, taurine, L-carnitine, and combinations thereof. Minerals are usually added in salt form.

Other suitable and desirable ingredients of maternal supplement composition, that may be employed in the compositions of the invention, are described in guidelines issued by the Codex Alimentarius.

The maternal supplement composition of the invention may be prepared in any way known in the art to prepare maternal supplements.

It is well within the purview of the skilled person to decide on a method depending on the type of maternal supplement in question e.g. powder or liquid.

In another aspect of the present invention there is provided a maternal supplement in accordance with the invention, for use in supplementing or fortifying human breast milk.

In an embodiment the human breast milk is breast milk from women who have given birth via C-section.

In one aspect, the present invention also provides for a maternal supplement composition as above described for use in preventing nutrient inadequacy in a woman who has delivered via C-section. Supplementing the nutrients who are decreased in HM of a woman who has delivered via C-section will thereby prevent nutrient inadequacy in her infant born via C-section.

In another embodiment, the present invention provides for a maternal supplement composition as above described for use in fortifying or supplementing the decreased amount of one or more nutrients that were observed to be decreased in HM, and preferably in HM produced by a woman who has delivered via C-section. Fortifying or supplementing HM produced by a woman who has delivered via C-section in one or more nutrients will thereby prevent nutrient inadequacy in her infant born via C-section.

The maternal supplement composition in accordance with the invention is tailored or adapted to complete or supplement the decreased amounts of one or more nutrients that were observed to be decreased in HM produced by mothers who have delivered via C-section, said one or more nutrients being selected in the list consisting of: ALA, DHA, EPA, vitamin A, thiamine, thiamine monophosphate, vitamin B2, vitamin B6, vitamin B9, phosphorus, and gangliosides In another aspect of the present invention there is provided a maternal supplement composition in accordance with the invention, for use to fortify or supplement the decreased amounts of one or more nutrients that were observed to be decreased in HM produced by a woman who has delivered via C-section thereby providing an optimised amount of one or more nutrients to an infant born via C-section and/or preventing the sub-optimal intake of one or more nutrients selected in the list consisting of: ALA, DHA, EPA, vitamin A, thiamine, thiamine monophosphate, vitamin B2, vitamin B6, vitamin B9, phosphorus, and gangliosides to an infant born via C-section. An optimised amount of one or more nutrients selected in the list consisting of: ALA, DHA, EPA, vitamin A, thiamine, thiamine monophosphate, vitamin B2, vitamin B6, vitamin B9, phosphorus, and gangliosides would be an amount equal to or greater than an amount e.g. the average amount, that an infant born by vaginal delivery would be considered to receive e.g. an amount of DHA set out in Table (included herein.

In one aspect, the present invention provides a maternal supplement composition as above described for use in i) preventing sub-optimal growth and development;
ii) preventing and/or treating inflammatory process;
iii) promoting cognitive development; and/or
iv) promoting immunity development in an infant born via C-section.

In another aspect of the present invention there is provided a maternal supplement composition in accordance with the invention, for use in preventing nutrient inadequacy in HM of a woman who has delivered via C-section, thereby preventing sub-optimal growth and development in an infant born via C-section. In one embodiment, there is provided a maternal supplement composition in accordance with the invention, for use in fortifying or supplementing the decreased amounts of one or more nutrients that were observed to be decreased in HM produced by a woman who has delivered via C-section, thereby optimising the health and development and/or preventing the sub-optimal health and development e.g. growth and development of an infant born via C-section.

In another aspect of the present invention there is provided a maternal supplement composition in accordance with the invention, for use in fortifying or supplementing the decreased amounts of one or more nutrients that were observed to be decreased in HM produced by a woman who has delivered via C-section thereby preventing sub-optimal growth and development in an infant born via C-section. In one embodiment, there is provided a maternal supplement composition in accordance with the invention, for use in fortifying or supplementing the decreased amounts of one or more nutrients that were observed to be decreased in HM produced by a woman who has delivered via C-section thereby optimising the health and development and/or preventing the sub-optimal health and development e.g. growth and development of an infant born via C-section.

The fortification of HM produced by a woman who has delivered via C-section resulting from the intake of the maternal supplement composition of the invention may not only optimise the health and development of an infant born via C-section short term but may also do so in the long term.

Long term effects may only be evident in months or years e.g. 6 months, 9 months, 12 months, 5 years, 10 years, or 20 years In another aspect of the present invention there is provided a maternal supplement composition in accordance with the invention, for use in preventing nutrient inadequacy in HM of a woman who has delivered via C-section, thereby preventing and/or treating inflammatory process in an infant born via C-section.

In another aspect of the present invention there is provided a maternal supplement composition in accordance with the invention, for use in fortifying or supplementing the decreased amounts of one or more nutrients that were observed to be decreased in HM produced by a woman who has delivered via C-section thereby preventing and/or treating inflammatory process in an infant born via C-section.

In another aspect of the present invention there is provided a maternal supplement composition in accordance with the invention, for use in preventing nutrient inadequacy in HM of a woman who has delivered via C-section, thereby promoting cognitive development in an infant born via C-section.

In another aspect of the present invention there is provided a maternal supplement composition in accordance with the invention, for use in fortifying or supplementing the decreased amounts of one or more nutrients that were observed to be decreased in HM produced by a woman who has delivered via C-section thereby promoting cognitive development in an infant born via C-section.

In another aspect of the present invention there is provided a maternal supplement composition in accordance with the invention, for use in preventing nutrient inadequacy in HM of a woman who has delivered via C-section, thereby promoting immunity development in an infant born via C-section.

In another aspect of the present invention there is provided a maternal supplement composition in accordance with the invention, for use in fortifying or supplementing the decreased amounts of one or more nutrients that were observed to be decreased in HM produced by a woman who has delivered via C-section thereby promoting immunity development in an infant born via C-section.

In another aspect, the present invention provides for a maternal supplement composition as described therein for use in preventing nutrient inadequacy in HM of a woman who has delivered via C-section, thereby reducing allergic outcome in infant born via C-section.

In a still further aspect, the present invention provides for a maternal supplement composition for use in fortifying or supplementing the amount of one or more nutrients that were observed to be decreased in HM, and preferably HM produced by a woman who has delivered via C-section, thereby reducing allergic outcome in infant born via C-section.

In one aspect of the present invention there is provided the use of a maternal supplement composition in accordance with the invention to supplement or the amount of one or more nutrients that were observed to be decreased in HM. Preferably, the HM is from a woman who has given birth via C-section.

In another aspect of the present invention there is provided the use of a maternal supplement composition in accordance with the invention, to supplement or fortify HM and to improve/prevent sub-optimal HM quality wherein said HM is from a woman who has given birth via C-section.

The quality of HM in a woman who has given birth via C-section may be considered sub-optimal if it comprises one or more nutrients selected in the list consisting of: ALA, DHA, EPA, vitamin A, thiamine, thiamine monophosphate, vitamin B2, vitamin B6, vitamin B9, phosphorus, and gangliosides in a concentration less than the concentration found in breast milk from a woman who has given birth vaginally e.g. in a concentration less than the average found in woman who have given birth vaginally.

Nutrients

Alpha Linolenic Acid (ALA)

In one embodiment of the present invention, a maternal supplement composition is provided which comprises ALA.

ALA may be incorporated in the composition of the invention as such or in the form of a physiologically acceptable derivative, such as a salt and/or by any source comprising ALA or any mixture thereof, such as oils enriched in ALA, seeds and nuts. In one embodiment, ALA is provided to the composition in the form of an oil enriched in such fatty acid.

As it is evident to the person skilled in the art, different ingredients may provide different amounts of ALA in the composition according to the present invention, depending on the nature and amount of the ingredient used. It will be nonetheless routine work to the skilled person to calculate the amount of ingredient needed to provide the claimed amount of ALA, based on the specification of the specific ingredient provided by the supplier.

In one embodiment, the maternal supplement or human milk fortifier composition of the present invention comprises ALA in an amount of at least 0.1 g/day. In another embodiment, the composition of the present invention comprises ALA in an amount ranging from 0.1 to 2.6 g/day.

In one embodiment, the maternal supplement composition of the present invention comprises ALA in an amount of at least 0.1 g. In another embodiment, the maternal supplement composition of the present invention comprises ALA in an amount ranging from 0.1 to 2.6 g.

In such embodiment, the maternal supplement composition of the present invention delivers in one serving or dosage unit the daily amount of ALA considered necessary to fill the gap of ALA between the human breast milk of a mother who delivered vaginally and that of a mother who delivered via C-section.

In one embodiment, the maternal supplement composition according to the present invention may be administered in 1, 2, 3 or 4 daily servings to provide the total daily amounts of ALA as above described. In such embodiment, as it will be apparent to a person skilled in the art, the amount of ALA contained in each serving of the maternal supplement composition according to the present invention will be divided by 1, 2, 3 or 4 respectively.

In one embodiment, the maternal supplement composition according to the present invention is intended for consumption once or twice per day.

Docosahexaenoic Acid (DHA)

In one embodiment of the present invention, a maternal supplement composition is provided which comprises DHA.

DHA may be incorporated in the maternal supplement composition of the invention as DHA or in the form of a physiologically acceptable derivative, such as a salt and/or by any source comprising DHA or any mixture thereof, such as for example oils enriched in DHA, algae or fish oil. In one embodiment, DHA is provided to the maternal supplement composition in the form of an oil enriched in such fatty acid.

As it is evident to the person skilled in the art, different ingredients may provide different amounts of DHA in the maternal supplement composition according to the present invention, depending on the nature and amount of the ingredient used. It will be nonetheless routine work to the skilled person to calculate the amount of ingredient needed to provide the claimed amount of DHA, based on the specification of the specific ingredient provided by the supplier.

In one embodiment, the maternal supplement composition of the present invention comprises DHA in an amount of at least 35 mg/day. In another embodiment, the maternal supplement composition of the present invention comprises DHA in an amount ranging from 35 to 700 mg/day.

In one embodiment, the maternal supplement composition of the present invention comprises DHA in an amount of at least 35 mg. In another embodiment, the maternal supplement composition of the present invention comprises DHA in an amount ranging from 35 to 700 mg.

In such embodiment, the maternal supplement composition of the present invention delivers in one serving or dosage unit, the daily amount of DHA considered necessary to fill the gap of DHA between the human breast milk of a mother who delivered vaginally and that of a mother who delivered via C-section.

In one embodiment, the maternal supplement composition according to the present invention may be administered in 1, 2, 3 or 4 daily servings to provide the total daily amounts of DHA as above described. In such embodiment, as it will be apparent to a person skilled in the art, the amount of DHA contained in each serving of the maternal supplement composition according to the present invention will be divided by 1, 2, 3 or 4 respectively.

In one embodiment, the maternal supplement composition according to the present invention is intended for consumption once or twice per day.

Eicosapentanoic Acid (EPA)

In one embodiment of the present invention, a supplement or human milk fortifier composition is provided which comprises EPA.

EPA may be incorporated in the maternal supplement composition of the invention as EPA or in the form of a physiologically acceptable derivative, such as a salt and/or by any source comprising EPA or any mixture thereof, such as for example oils enriched in EPA, algae or fish oil. In one embodiment, EPA is provided to the maternal supplement composition in the form of an oil enriched in such fatty acid.

As it is evident to the person skilled in the art, different ingredients may provide different amounts of EPA in the maternal supplement composition according to the present invention, depending on the nature and amount of the ingredient used. It will be nonetheless routine work to the skilled person to calculate the amount of ingredient needed to provide the claimed amount of EPA, based on the specification of the specific ingredient provided by the supplier.

In one embodiment, the maternal supplement composition of the present invention comprises EPA in an amount of at least 10 mg/day. In another embodiment, the maternal supplement composition of the present invention comprises EPA in an amount ranging from 10 to 200 mg/day.

In one embodiment, the maternal supplement composition of the present invention comprises EPA in an amount of at least 10 mg. In another embodiment, the maternal supplement composition of the present invention comprises EPA in an amount ranging from 10 to 200 mg.

In such embodiment, the maternal supplement composition of the present invention delivers in one serving the daily amount of EPA considered necessary to fill the gap of EPA between the human breast milk of a mother who delivered vaginally and that of a mother who delivered via C-section.

In one embodiment, the maternal supplement composition according to the present invention may be administered in 1, 2, 3 or 4 daily servings to provide the total daily amounts of EPA as above described. In such embodiment, as it will be apparent to a person skilled in the art, the amount of EPA contained in each serving of the maternal supplement composition according to the present invention will be divided by 1, 2, 3 or 4 respectively.

In one embodiment, the maternal supplement composition according to the present invention is intended for consumption once or twice per day.

Gangliosides

In one embodiment of the present invention, a maternal supplement composition is provided which comprises gangliosides. Gangliosides include but are not limited to common gangliosides such as, GM1, GM2, GM3, GD1a, GD1b, GD2, GD3.

Gangliosides may be incorporated in the maternal supplement or human milk fortifier composition of the invention as such or in the form of a physiologically acceptable derivative, such as a salt and/or by any source comprising gangliosides or any mixture thereof, such as dairy ingredients (such as milk fat globule membrane and whey protein), meat, fish, animal derived ingredients. In one embodiment, gangliosides are provided as such to the maternal supplement composition.

As it is evident to the person skilled in the art, different ingredients may provide different amounts of gangliosides in the maternal supplement composition according to the present invention, depending on the nature and amount of the ingredient used. It will be nonetheless routine work to the skilled person to calculate the amount of ingredient needed to provide the claimed amount of gangliosides, based on the specification of the specific ingredient provided by the supplier.

In one embodiment, the maternal supplement composition of the present invention comprises gangliosides in an amount of at least 0.1 mg/day. In another embodiment, the composition of the present invention comprises GD3 in an amount ranging from 0.1 to 12.6 mg/day.

In one embodiment, the maternal supplement composition of the present invention comprises gangliosides in an amount of at least 0.1 mg. In another embodiment, the maternal supplement composition of the present invention comprises gangliosides in an amount ranging from 0.1 to 12.6 mg.

In such embodiment, the maternal supplement composition of the present invention delivers in one serving the daily amount of gangliosides considered necessary to fill the gap of gangliosides between the human breast milk of a mother who delivered vaginally and that of a mother who delivered via C-section.

In one embodiment, the maternal supplement composition according to the present invention may be administered in 1, 2, 3 or 4 daily servings to provide the total daily amounts of gangliosides as above described. In such embodiment, as it will be apparent to a person skilled in the art, the amount of gangliosides contained in each serving of the maternal supplement composition according to the present invention will be divided by 1, 2, 3 or 4 respectively.

In one embodiment, the maternal supplement composition according to the present invention is intended for consumption once or twice per day.

Vitamin B6

In one embodiment of the present invention, a maternal supplement composition is provided which comprises vitamin B6.

Vitamin B6 may be incorporated in the maternal supplement or composition according to the present invention as such or in the form of a physiologically acceptable salt and/or by any source comprising vitamin B6. For example, ingredients may be selected in the group consisting of pyridoxine (in the form of pyridoxine hydrochloride [HCl]) and pyridoxal 5' phosphate (PLP).

As it is evident to the person skilled in the art, different ingredients may provide different amounts of vitamin B6 in the maternal supplement composition according to the present invention, depending on the nature and amount of the ingredient used. It will be nonetheless routine work to the skilled person to calculate the amount of ingredient needed to provide the claimed amount of vitamin B6, based on the specification of the specific ingredient provided by the supplier.

In one embodiment, the maternal supplement composition comprises vitamin B6 is an amount of at least 0.2 mg/day. In a still further embodiment, the maternal supplement composition comprises vitamin B6 in an amount ranging from 0.2 to 100 mg/day.

In one embodiment, the maternal supplement composition comprises vitamin B6 is an amount of at least 0.2 mg. In a still further embodiment, the composition maternal supplement or human milk fortifier comprises vitamin B6 in an amount ranging from 0.2 to 100 mg.

In such embodiment, the maternal supplement composition of the present invention delivers in one serving the daily amount of vitamin B6 considered necessary to fill the gap of vitamin B6 between the human breast milk of a mother who delivered vaginally and that of a mother who delivered via C-section.

In one embodiment, the maternal supplement composition according to the present invention may be administered in 1, 2, 3 or 4 daily servings to provide the total daily amounts of vitamin B6 as above described. In such embodiment, as it will be apparent to a person skilled in the art, the amount of vitamin B6 contained in each serving or dosage unit of the composition maternal supplement according to the present invention will be divided by 1, 2, 3 or 4 respectively.

In one embodiment, the composition maternal supplement according to the present invention is intended for consumption once or twice per day.

Vitamin B2 (Riboflavin)

In one embodiment of the present invention, a maternal supplement or composition is provided which comprises vitamin B2.

Vitamin B2 may be incorporated in the maternal supplement composition of the invention as such or in the form of a physiologically acceptable salt and/or by any source comprising Vitamin B2. For example, ingredients may be selected in the group consisting of riboflavin and riboflavin 5'-monophosphate.

As it is evident to the person skilled in the art, different ingredients may provide different amounts of vitamin B2 in the composition according to the present invention, depending on the nature and amount of the ingredient used. It will be nonetheless routine work to the skilled person to calculate the amount of ingredient needed to provide the claimed amount of vitamin B2, based on the specification of the specific ingredient provided by the supplier.

In one embodiment, the maternal supplement composition comprises vitamin B2 in an amount of at least 0.16 mg/day. In a further embodiment, the maternal supplement composition comprises vitamin B2 in an amount ranging from 0.16 to 3.2 mg/day.

In one embodiment, the maternal supplement composition comprises vitamin B2 in an amount of at least 0.16 mg. In a further embodiment, the maternal supplement composition comprises vitamin B2 in an amount ranging from 0.16 mg to 3.2 mg.

In such embodiment, the maternal supplement composition of the present invention delivers in one serving the daily amount of vitamin B2 considered necessary to fill the gap of vitamin B2 between the human breast milk of a mother who delivered vaginally and that of a mother who delivered via C-section.

In one embodiment, the maternal supplement composition according to the present invention may be administered in 1, 2, 3 or 4 daily servings to provide the total daily amounts of vitamin B2 as above described. In such embodiment, as it will be apparent to a person skilled in the art, the amount of vitamin B2 contained in each serving or dosage unit of the maternal supplement composition according to the present invention will be divided by 1, 2, 3 or 4 respectively.

In one embodiment, the maternal supplement composition according to the present invention is intended for consumption once or twice per day.

Thiamine (Vitamin B1)

In one embodiment of the present invention, a maternal supplement composition is provided which comprises thiamine.

Thiamine may be incorporated in the maternal supplement composition of the invention as such or in the form of a physiologically acceptable salt and/or by any source comprising thiamine. For example, ingredients may be selected in the group consisting of thiamine mononitrate and thiamine hydrochloride.

As it is evident to the person skilled in the art, different ingredients may provide different amounts of thiamine in the maternal supplement composition according to the present invention, depending on the nature and amount of the ingredient used. It will be nonetheless routine work to the skilled person to calculate the amount of ingredient needed to provide the claimed amount of thiamine, based on the specification of the specific ingredient provided by the supplier.

In one embodiment, the maternal supplement composition comprises thiamine in an amount of at least 0.14 mg/day. In a further embodiment, the maternal supplement composition comprises thiamine in an amount ranging from 0.14 mg/day to 2.8 mg/day.

In one embodiment, the maternal supplement composition comprises thiamine in an amount of at least 0.14 mg. In a further embodiment, the maternal supplement composition comprises thiamine in an amount ranging from 0.14 mg to 2.8 mg.

In such embodiment, the maternal supplement composition of the present invention delivers in one serving the daily amount of thiamine considered necessary to fill the gap of thiamine between the human breast milk of a mother who delivered vaginally and that of a mother who delivered via C-section.

In one embodiment, the maternal supplement composition according to the present invention may be administered in 1, 2, 3 or 4 daily servings to provide the total daily amounts of thiamine as above described. In such embodiment, as it will be apparent to a person skilled in the art, the amount of thiamine contained in each serving or dosage unit of the maternal supplement composition according to the present invention will be divided by 1, 2, 3 or 4 respectively.

In one embodiment, the maternal supplement composition according to the present invention is intended for consumption once or twice per day.

Thiamine Monophosphate

Thiamine monophosphate may be incorporated in the maternal supplement composition of the invention as such or in the form of a physiologically acceptable salt and/or by any source comprising thiamine monophosphate. For example, ingredients may be selected in the group consisting of thiamine mononitrate and thiamine hydrochloride.

As it is evident to the person skilled in the art, different ingredients may provide different amounts of thiamine monophosphate in the maternal supplement composition according to the present invention, depending on the nature and amount of the ingredient used. It will be nonetheless routine work to the skilled person to calculate the amount of ingredient needed to provide the claimed amount of thiamine monophosphate, based on the specification of the specific ingredient provided by the supplier.

In one embodiment, the maternal supplement composition comprises thiamine monophosphate in an amount of at least 0.14 mg/day. In a further embodiment, the maternal supplement composition comprises thiamine monophosphate in an amount ranging from 0.14 mg/day to 2.8 mg/day.

In one embodiment, the maternal supplement composition comprises thiamine monophosphate in an amount of at least 0.14 mg. In a further embodiment, the maternal supplement composition comprises thiamine monophosphate in an amount ranging from 0.14 mg to 2.8 mg.

In such embodiment, the maternal supplement composition of the present invention delivers in one serving the daily amount of thiamine monophosphate considered necessary to fill the gap of thiamine monophosphate between the human breast milk of a mother who delivered vaginally and that of a mother who delivered via C-section.

In one embodiment, the maternal supplement composition according to the present invention may be administered in 1, 2, 3 or 4 daily servings to provide the total daily amounts of thiamine monophosphate as above described. In such embodiment, as it will be apparent to a person skilled in the art, the amount of thiamine monophosphate contained in each serving or dosage unit of the maternal supplement composition according to the present invention will be divided by 1, 2, 3 or 4 respectively.

In one embodiment, the maternal supplement composition according to the present invention is intended for consumption once or twice per day.

Phosphorus

In one embodiment of the present invention, a maternal supplement composition is provided which comprises phosphorus.

Phosphorus may be incorporated in the maternal supplement of the invention in the form of a physiologically acceptable salt and/or by any source comprising phosphorus. For example, phosphorous may be comprised in the form of sodium phosphate.

As it is evident to the person skilled in the art, different ingredients may provide different amounts of phosphorous in the maternal supplement composition according to the present invention, depending on the nature and amount of the ingredient used. It will be nonetheless routine work to the skilled person to calculate the amount of ingredient needed to provide the claimed amount of phosphorous, based on the specification of the specific ingredient provided by the supplier.

In one embodiment, the maternal supplement composition of the present invention comprises phosphorus in an amount of at least 70 mg/day. In another embodiment, the maternal supplement composition of the present invention comprises phosphorus in an amount ranging from 70 to 4000 mg/day.

In one embodiment, the maternal supplement composition of the present invention comprises phosphorus in an amount of at least 70 mg. In another embodiment, the maternal supplement composition of the present invention comprises phosphorus in an amount ranging from 70 to 4000 mg.

In such embodiment, the maternal supplement composition of the present invention delivers in one serving the daily amount of phosphorous considered necessary to fill the gap of phosphorous between the human breast milk of a mother who delivered vaginally and that of a mother who delivered via C-section.

In one embodiment, the maternal supplement composition according to the present invention may be administered in 1, 2, 3 or 4 daily servings to provide the total daily amounts of phosphorous as above described. In such embodiment, as it will be apparent to a person skilled in the art, the amount of phosphorous contained in each serving or dosage unit of the maternal supplement composition according to the present invention will be divided by 1, 2, 3 or 4 respectively.

In one embodiment, the maternal supplement composition according to the present invention is intended for consumption once or twice per day.

Vitamin A

In one embodiment of the present invention, a maternal supplement is provided which comprises vitamin A.

Vitamin A may be incorporated in the maternal supplement composition of the invention as such or in the form of a physiologically acceptable derivative such as a salt and/or by any source comprising vitamin A. For example ingredients may be selected in the group consisting of: carrots, red sweet peppers, turnips, orange juice, oranges, tomatoes, dark green leafy vegetables (such as spinach, broccoli and kale), cantaloupe, oranges, tomatoes, apricot, plantains, mangos, passion fruits, squash, yellow corn, soybeans, pistachio nuts, egg yolk, butter, milk, liver, cod liver oil and mixtures thereof. Vitamin pre-mix for fortification purpose is also included.

In one embodiment, vitamin A is provided as such to the maternal supplement composition.

As it is evident to the person skilled in the art, different ingredients may provide different amounts of vitamin A in the maternal supplement composition according to the present invention, depending on the nature and amount of the ingredient used. It will be nonetheless routine work to the skilled person to calculate the amount of ingredient needed to provide the claimed amount of vitamin A, based on the specification of the specific ingredient provided by the supplier.

In one embodiment, the maternal supplement composition comprises vitamin A in an amount of at least 130 μg/day. In a further embodiment, the maternal supplement or human milk fortifier composition comprises vitamin A in an amount ranging from 130 μg/day to 3000 μg/day.

In one embodiment, the maternal supplement composition comprises vitamin A in an amount of at least 130 μg. In a further embodiment, the maternal supplement or human milk fortifier composition comprises vitamin A in an amount ranging from 130 μg to 3000 μg.

In such embodiment, the maternal supplement composition of the present invention delivers in one serving the daily amount of vitamin A considered necessary to fill the gap of vitamin A between the human breast milk of a mother who delivered vaginally and that of a mother who delivered via C-section.

In one embodiment, the maternal supplement composition according to the present invention may be administered in 1, 2, 3 or 4 daily servings to provide the total daily amounts of vitamin A as above described. In such embodiment, as it will be apparent to a person skilled in the art, the amount of vitamin A contained in each serving of the maternal supplement composition according to the present invention will be divided by 1, 2, 3 or 4 respectively.

In one embodiment, the maternal supplement composition according to the present invention is intended for consumption once or twice per day.

Vitamin B9 (Folate or Folic Acid)

In one embodiment of the present invention, a maternal supplement is provided which comprises vitamin B9.

Vitamin B9 may be incorporated in the maternal supplement composition of the invention as folic acid or in the form of a physiologically acceptable derivative, such as a salt and/or by any source comprising vitamin B9 or any mixture thereof, such as leafy green vegetables, (such as spinach, broccoli, and lettuce), beans, peas, and lentils, fruits (such as lemons, bananas, and melon). In one embodiment, vitamin B9 is provided as such to the composition.

As it is evident to the person skilled in the art, different ingredients may provide different amounts of vitamin B9 in the maternal supplement composition according to the present invention, depending on the nature and amount of the ingredient used. It will be nonetheless routine work to the skilled person to calculate the amount of ingredient needed to provide the claimed amount of vitamin B9, based on the specification of the specific ingredient provided by the supplier.

In one embodiment, the maternal supplement composition comprises vitamin B9 in an amount of at least 50 μg/day. In a further embodiment, the maternal supplement or human milk fortifier composition comprises vitamin B9 in an amount ranging from 50 μg/day to 1000 μg/day.

In one embodiment, the maternal supplement composition comprises vitamin B9 in an amount of at least 50 [lg. In a further embodiment, the maternal supplement or human milk fortifier composition comprises vitamin B9 in an amount ranging from 50 μg to 1000 i.tg.

In such embodiment, the maternal supplement composition of the present invention delivers in one serving the daily amount of vitamin B9 considered necessary to fill the gap of vitamin B9 between the human breast milk of a mother who delivered vaginally and that of a mother who delivered via C-section.

In one embodiment, the maternal supplement composition according to the present invention may be administered in 1, 2, 3 or 4 daily servings to provide the total daily amounts of vitamin B9 as above described. In such embodiment, as it will be apparent to a person skilled in the art, the amount of vitamin B9 contained in each serving or dosage unit of maternal supplement composition according to the present invention will be divided by 1, 2, 3 or 4 respectively.

In one embodiment, the maternal supplement composition according to the present invention is intended for consumption once or twice per day.

Method

In one aspect of the present invention, there is provided a method of mitigating nutrient inadequacy in a woman who has delivered via C-section, said method comprising:

i) identifying the gap in certain nutrients between the human breast milk composition from mothers who have delivered via C-section and the human breast milk composition from mothers who have delivered vaginally;

ii) providing a maternal supplement according to the present invention to mitigate the identified nutritional inadequacies in a woman who has delivered via C-section.

The identification of the gap in certain nutrients, resulting in nutrient inadequacy, results from the comparative analysis between the HM composition of mothers who delivered vaginally versus the HM composition of women who delivered via C-section, using suitable statistical methods known by the skilled person. The analysis of the HM composition may be performed at any period during the breast-feeding period.

The maternal supplement may be provided to the mother who has delivered via C-section at any period while she is breast-feeding.

It should be appreciated that all features of the present invention disclosed herein can be freely combined and that variations and modifications may be made without departing from the scope of the invention as defined in the claims. Furthermore, where known equivalents exist to specific features, such equivalents are incorporated as if specifically referred to in this specification.

There now follows a series of non-limiting examples that serve to illustrate the invention.

EXAMPLES

Example 1

Four cohorts were evaluated to study differences between the HM composition of mothers who delivered vaginally versus those who delivered via C-section. A brief overview and description of these cohorts are provided in Table II, followed by a more description of the protocol and analysis performed for each of the studies.

TABLE II

| | Study 1<br>Europe<br>NCT01894893 | Study 2<br>Singapore<br>NCT01805011 | Study 3 | Study 4<br>Preemie<br>NCT02052245 |
|---|---|---|---|---|
| Study design | Longitudinal cohort study | Longitudinal cohort study | Cross sectional cohort study | Longitudinal cohort study |
| Duration of follow up | 4 months postpartum | 4 months postpartum | 8 months postpartum | 4 months postpartum |
| Population | European | Singaporean | Chinese | Swiss |
| Sample size used for the above analyses (with a split between the 2 groups) | C-section: 80<br>Vaginal: 237 | C-section: 19<br>Vaginal: 31 | C-section:<br>0-4 days 65<br>5-11 days 46<br>12-30 days 43<br>1-2 months 57<br>2-4 months 35<br>4-8 months 34<br>Vaginal:<br>0-4 days 45<br>5-11 days 50<br>12-30 days 47<br>1-2 months 41<br>2-4 months 55<br>4-8 months 55 | C-section: 8<br>Vaginal: 20 |

Study 1 (NCT01894893)

Study Population

Study 1 is a multicentre, longitudinal, observational, exploratory cohort study designed to characterize HM and its association with maternal and infant parameters. HM as well as multiple maternal and infant parameters were collected postpartum at 6 visits (V) (V1, 0-3 days; V2, 17±3 days; V3, 30±3 days; V4, 60±5 days; V5, 90±5 days; V6, 120±5 days). Enrolment was performed at multiple sites in 7 European countries, including Spain, France, Italy, Norway, Portugal, Romania, and Sweden. The total duration of participation was 4 months after infant birth. Trained and certified research nurses and assistants collected all data. All data captured were directly entered into a secured web-based database (Medidata Rave edc 5.6.4). The procedures followed were in accordance with the ethical standards of the respective local ethical committees in each country.

Analysis Population

A total of 370 participants from 7 European countries including Spain (1 center), France (3 centers), Italy (1 center), Norway (1 center), Portugal (3 centers), Romania (2 centers), and Sweden (2 centers) were enrolled for this study and included in the dataset. Participants were counted as pairs of mothers and infants. The analysis was performed on 317 participants (pairs) after removal of pairs who did not satisfy the inclusion-exclusion criteria, pairs with twins and with incomplete information on HM composition Statistical Methods A total of 62 components were considered for this analysis. Values below the level of quantification for a given parameter were replaced by half of the corresponding level of quantification.

To compare levels of the milk components between delivery modes at each visit, two-sided Mann-Whitney U tests were performed. Additionally, to account for confounders, a targeted approach (mixed model) was fitted to each of these 62 components. Such a model was fitted on the log-transformed data to achieve approximate normality of the residuals. Individuals (pairs of a mother and her child) were considered as random effects and the following covariates were considered as fixed effects in the mixed model: visit, delivery mode and the interaction between the two latter. In addition, mother's country, infant's weight at VO (child's birth), parity, and gestational age were considered as potential confounders and were also added as fixed effects. Due to the log transformation, group differences between delivery modes were computed per visit and were expressed as ratio of geometric means between the vaginal group and the C-section group. Hence, a model-based estimate higher than 1 means that the estimation (geometric mean) is higher in the vaginal group than in C-section group, while an estimate below 1 means that levels of the corresponding parameter are higher in the C-section group. $P<0.05$ was considered statistically significant.

NTF (Non-Negative Tensor Factorization)

Non-NTF is a non-supervised approach dedicated to the analysis of longitudinal datasets [25]. Specifically, NTF estimates several factors along the three dimensions of the data space: Participant×Visit×HM component. Each NTF factor represents a particular trend (e.g. increase/decrease). Participant and parameter loadings along each NTF factor reflect the level of similarity for a given participant and parameter with one trend or another. NTF factor loadings are subsequently used to build bi-clusters of participants and milk parameters sharing similar trends. To guide the NTF analysis for greater focus on mode of delivery, pre-selected nutrients were included. Repeated ANOVA with the delivery mode as a main effect on 62 milk nutrients (log-transformed), using JMP version 14.2 (SAS Institute) was conducted to pre-select those nutrients. Participants with missing time points or data were excluded in the repeated ANOVA. In this way, only nutrients were analyzed by NTF that showed some degree of association with the mode of delivery.

Study 2 (NCT01805011)

Study Population

Study 2 is an open, single-centre, 1 group study on Singaporean healthy lactating mothers. Milk samples (and other infant parameters) were collected at 3 postpartum visits: 1 month (V1), 2 months (V2) and 4 months (V3) after delivery.

Analysis Population

The analysis was performed on all 50 enrolled mothers (and their child, no twins). Statistical methods A total of 60 human milk components were considered for this analysis. Values below the level of quantification for a given parameter were replaced by half of the corresponding level of quantification.

Levels of milk components were compared between delivery modes at each visit by a (two-sided) Wilcoxon rank-sum test. The resulting p-value was reported alongside an estimate of the difference in location between the two groups and a 95% confidence interval of this difference (see the documentation of wilxocon test function from R package stats).

Comparison of maternal and infant characteristics between delivery modes was performed as follows: for continuous variables a (two-sided) Wilcoxon rank sum test was used to test the null hypothesis that the distributions of C-section and Vaginal have the same location (which amounts to compare their medians if their distributions are symmetric). For categorical variables a Pearson's chi-squared test is used to test the null hypothesis that delivery mode is independent from the current categorical variable (i.e. if the proportions in mode of delivery are independent from the proportions of the categorical variable). If a categorical variable has only one level (with non-missing value), then no test was performed.

Given the exploratory nature of the study no multiplicity adjustment was performed and $P<0.05$ was considered statistically significant.

Study 3

Study Population

This is an observational, cross sectional, multi-centre study aiming at evaluating nutrients composition of breast milk and nutrition intake of Chinese lactating mothers in 3 cities of China (Beijing, Suzhou and Guangzhou). In Beijing, Suzhou and Guangzhou there were 220, 180 and 180 of healthy lactating mothers respectively, enrolled at different lactation stages (within 0-4 days, 5-11 days, 12-30 days, 31-60 days, 61-120 days and 121-240 days postpartum). In total, 580 mothers were enrolled.

Analysis Population 580 mothers were enrolled in the study. The analysis was performed on a subset of 573 mothers (and their child, no twins) who delivered via C-section or by natural birth. Among the 7 mothers that were not included in this analysis: for 3 of them the delivery method is not specified and 4 of them delivered with dystocia of normal labour.

Statistical Methods

The same methodology than in Study 2 was employed except that here comparisons between delivery modes are performed within each lactating stage on 133 human milk components.

Study 4 (NCT02052245)

Study Population

Open, single-center, exploratory study on healthy lactating mothers delivering term (gestational age (hereinafter "ga") between 37 and not above 42 weeks) and preterm (ga between 28 and 32 weeks) infants. A total of 61 mothers (34 in the term group and 25 in the preterm group, 6 mothers in the latter group delivered twins) were enrolled in the study. For subjects who delivered pre-term babies, milk samples were collected once a week until discharge from hospital and then every 2 weeks until 8 weeks after birth (at most 12 visits post-screening). For subjects who delivered term babies, milk samples were collected once a week until 8 weeks after birth (8 visits post-screening).

Analysis Population

This analysis focused on mothers delivering term infants. Hence, out of the 61 enrolled mothers, the 34 mothers from the term group were considered in this analysis. Following the study protocol, from this population we further removed 6 mothers who dropped out of the study and hence ended up with 28 mothers for the analysis, all of which have delivered unique infants (no multiple births).

Statistical Methods

The same methodology than in Study 2 was employed. Here, 120 human milk components were considered for analysis.

Table III reports the results of such analysis, showing the gap in certain nutrients between the HM composition from mothers who have delivered via C-section and the HM composition from mothers who have delivered vaginally. Table III also reports the recommended daily intake for each nutrient which would be necessary to close the gap for such nutrients' content in human breast milk received babies born via C-section versus human breast milk received by infants born vaginally, considering that global average human milk consumption is 780 ml/day.

TABLE III

| Nutrients | Direction of effect | Observed in how many cohorts and at what time points | Median concentrations in HM: Vaginal | Median concentrations in HM: C-section | p- value | Daily amount to be supplemented |
|---|---|---|---|---|---|---|
| **Fatty acids** | | | | | | |
| ALA (18:3 n-3) | Lower in C section HM | Study 1 v1 (2 days) | 13.6 (mg/100 ml) | 10.6 (mg/100 ml) | ≤0.01 | 23.4 mg/d |
| ALA (18:3 n-3) | Lower in C section HM | Study 1 v2 (17 days) | 21.1 (mg/100 ml) | 15.7 (mg/100 ml) | ≤0.01 | 41.34 mg/d |
| ALA (18:3 n-3) | Lower in C section HM | Study 1 v3 (30 days) | 22.7 (mg/100 ml) | 15.5 (mg/100 ml) | ≤0.01 | 56.16 |
| ALA (18:3 n-3) | Lower in C section HM | Study 1 v5 (90 days) | 23.1 (mg/100 ml) | 15.1 (mg/100 ml) | ≤0.01 | 62.4 mg/d |
| ALA (18:3 n-3) | Lower in C section HM | Study 1 v6 (120 days) | 23.6 (mg/100 ml) | 15.1 (mg/100 ml) | ≤0.01 | 66.3 mg/d |
| DHA (22:6 n-3) | Lower in C section HM | Study 1 v1 (2 days) | 11 (mg/100 ml) | 8.3 (mg/100 ml) | 0.01 < p ≤ 0.05 | 21.06 mg/d |
| DHA (22:6 n-3) | Lower in C section HM | Study 1 v3 (30 days) | 11.2 (mg/100 ml) | 9.1 (mg/100 ml) | 0.01 < p ≤ 0.05 | 16.38 mg/d |
| EPA (20:5 n-3) | Lower in C section HM | Study 1 v3 (30 days) | 2.02 (mg/100 ml) | 1.0 (mg/100 ml) | 0.01 < p ≤ 0.05 | 7.8 mg/d |
| **Gangliosides** | | | | | | |
| $GD_3$ | Lower in C section HM | Study 1 v1 (2 days) | 7.7 (mg/ml) | 6.4 (mg/ml) | 0.01 < p ≤ 0.05 | 10.14 mg/d |
| $GM_3$ | Lower in C section HM | Study 3 v1 (0 to 4 days) | 0.73 (mg/ml) | 0.58 (mg/ml) | 0.01 | 1.199 mg/d |
| **Micronutrients** | | | | | | |
| Vitamin A | Lower in C section HM | Study 3 (0 to 4 days) | 148 (µg/100 m) | 764 (µg/100 m) | 0.02 | 280.8 µg/d |
| | | Study 4 V6 (week 6) | 90 (µg/100 ml) | 53 (µg/100 ml) | 0.04 | 285 µg/d |
| Thiamine | Lower in C section HM | Study 4 V3 (week 3) | 1.32 (µg/100 ml) | 0.25 (µg/100 ml) | 0.03 | 8.34 µg/d |
| Thiamine monophosphate | Lower in C section HM | Study 4 V2 (week 2) | 6.40 (µg/100 ml) | 4.83 (µg/100 ml) | 0.04 | 12.2 µg/d |

TABLE III-continued

| Nutrients | Direction of effect | Observed in how many cohorts and at what time points | Median concentrations in HM Vaginal | C-section | p- value | Daily amount to be supplemented |
|---|---|---|---|---|---|---|
| Vitamin B2 (Riboflavin) | Lower in C section HM | Study 4 V4 (week 4) | 3.82 (µg/100 ml) | 2.40 (µg/100 ml) | 0.04 | 11.0 µg/d |
| | Lower in C section HM | Study 4 V5 (week 5) | 3.31 (µg/100 ml) | 1.24 (µg/100 ml) | 0.00 | 16.1 µg/d |
| Vitamin B6 | Lower in C section HM | Study 4 V2 (week 2) | 4.20 (µg/100 ml) | 1.83 (µg/100 ml) | 0.04 | 18.4 µg/d |
| | Lower in C section HM | Study 4 V5 (week 5) | 12.86 (µ/100 ml) | 5.52 (µg/100 ml) | 0.02 | 57.2 µg/d |
| Vitamin B9 | Lower in C section HM | Study 4 V3 (week 3) | 1.07 (µ/100 ml) | 0.10 (µg/100 ml) | 0.02 | 7.56 µg/d |
| | Lower in C section HM | Study 4 V4 (week 4) | 0.33 (µ/100 ml) | 0.10 (µg/100 ml) | 0.03 | 1.79 µg/d |
| | Lower in C section HM | Study 4 V5 (week 5) | 0.28 (µ/100 ml) | 0.10 (µg/100 ml) | 0.04 | 1.40 µg/d |
| | Lower in C section HM | Study 4 V8 (week 8) | 0.70 (µ/100 ml) | 0.10 (µg/100 ml) | 0.02 | 4.68 µg/d |
| Phosphorus | Lower in C section HM | Study 1 V1 (2 days) | 1.27 (mg/l) | 113 (mg/l) | <0.05 | 11.1 mg/d |
| | | Study 1 V1 (2 days) | 132 (mg/l) | 125 (mg/l) | <0.05 | 5.4 mg/d |

All publications mentioned in the above specification are herein incorporated by reference. Various modifications and variations of the disclosed methods, compositions and uses of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention claimed is:

1. A maternal supplement composition comprising alpha linolenic acid (ALA) in a daily amount ranging from 0.1 to 2.6 mg;

docosahexaenoic acid (DHA) in a daily amount ranging from 35 to 700 mg;

eicosapentanoic acid (EPA) in a daily amount ranging from 10 to 200 mg.

2. The maternal supplement composition according to claim 1 which also comprises at least one nutrient selected from the group consisting of:

vitamin A in a daily amount ranging from 130 to 3000 µg;

thiamin in a daily amount ranging from 0.14 to 2.8 mg;

thiamin monophosphate in a daily amount ranging from 0.14 to 2.8 mg;

vitamin B2 in a daily amount ranging from 0.16 to 3.2 mg;

vitamin B6 in a daily amount ranging from 0.2 to 100 mg;

vitamin B9 in a daily amount ranging from 50 to 1000 µg;

phosphorus in a daily amount ranging from 70 to 4000 mg; and gangliosides in a daily amount ranging from 0.1 to 12.6 mg.

3. The maternal supplement composition according to claim 1 which further comprises at least one nutrient selected from the group consisting of phosphorus in a daily amount ranging from 70 to 4000 mg; and gangliosides in a daily amount ranging from 0.1 to 12.6 mg.

4. The maternal supplement composition according to claim 1, wherein the daily amount of each of the nutrient is provided by 1 dosage unit or serving of the maternal supplement composition.

5. The maternal supplement composition according to claim 1, wherein the maternal supplement composition further comprises one or more ingredient selected from the group consisting of additional vitamins, additional minerals, protein, additional carbohydrates, and probiotics.

6. The maternal supplement composition according to claim 5, wherein the maternal supplement composition further comprises one or more probiotics selected from the group consisting of *Bifidobacterium longum* NCC3001 (ATCC BAA-999), *Bifidobacterium longum* NCC2705 (CNCM 1-2618), *Bifidobacterium longum* NCC490 (CNCM 1-2170), *Bifidobacterium lactis* NCC2818 (CNCM 1-3446), *Bifidobacterium breve* strain A, *Lactobacillus paracasei* NCC2461 (CNCM 1-2116), *Lactobacillus johnsonfi* NCC533 (CNCM 1-1225), *Lactobacillus rhamnosus* GG (ATCC53103), *Lactobacillus rhamnosus* NCC4007 (CGMCC 1.3724), and *Enterococcus faecium* SF 68 (NCC2768; NCIMB10415).

7. The maternal supplement composition according to claim 5, wherein the maternal supplement composition further comprises one or more proteins selected from the group consisting of casein, alpha-lactalbumin, whey, soy protein, rice protein, corn protein, oat protein, barley protein, wheat protein, rye protein, pea protein, egg protein, sunflower seed protein, potato protein, fish protein, meat protein, lactoferrin, serum albumin, and immunoglobins.

8. The maternal supplement composition according to claim 5, wherein the maternal supplement composition further comprises additional carbohydrates selected from the group consisting of lactose, saccharose, maltodextrin, starch, and combinations thereof.

9. A method of mitigating nutrient inadequacy in a woman who has delivered an infant via C-section, the method comprising:

i) identifying a gap in nutrients between human breast milk compositions from mothers who have delivered via C-section and human breast milk compositions from mothers who have delivered vaginally; and ii) administering to the woman who has delivered the infant via C-section a maternal supplement composition comprising alpha linolenic acid (ALA) in a daily amount ranging from 0.1 to 2.6 mg;

docosahexaenoic acid (DHA) in a daily amount ranging from 35 to 700 mg;

eicosapentanoic acid (EPA) in a daily amount ranging from 10 to 200 mg, wherein the administering of the maternal supplement composition mitigates identified nutritional inadequacies in the woman who has delivered via C-section.

10. The method according to claim 9, wherein the administering of the maternal supplement composition i) prevents sub-optimal growth and development;

ii) prevents and/or treats inflammatory process;

iii) promotes cognitive development; and/or iv) promotes immunity development, in the infant born from the woman via C-section.

11. The method according to claim 9, wherein the infant is selected from the group consisting of preterm infants and term infants.

12. The method of claim 9, wherein the maternal supplement composition further comprises at least one nutrient selected from the group consisting of:

vitamin A in a daily amount ranging from 130 to 3000 μg;

thiamin in a daily amount ranging from 0.14 to 2.8 mg;

thiamin monophosphate in a daily amount ranging from 0.14 to 2.8 mg;

vitamin B2 in a daily amount ranging from 0.16 to 3.2 mg;

vitamin B6 in a daily amount ranging from 0.2 to 100 mg;

vitamin B9 in a daily amount ranging from 50 to 1000 μg;

phosphorus in a daily amount ranging from 70 to 4000 mg; and gangliosides in a daily amount ranging from 0.1 to 12.6 mg.

* * * * *